(12) United States Patent
Groeller et al.

(10) Patent No.: US 8,094,004 B2
(45) Date of Patent: Jan. 10, 2012

(54) TURN SIGNAL DEVICE SELF CANCELLING FEATURE

(75) Inventors: Charles J. Groeller, Orefield, PA (US); Joseph Deevy, Harleysville, PA (US)

(73) Assignee: Mack Trucks, Inc., Greensboro, NC (US)

( * ) Notice: Subject to any disclaimer, the term of this patent is extended or adjusted under 35 U.S.C. 154(b) by 357 days.

(21) Appl. No.: 12/448,576

(22) PCT Filed: Jul. 18, 2007

(86) PCT No.: PCT/US2007/016272
§ 371 (c)(1),
(2), (4) Date: Sep. 25, 2009

(87) PCT Pub. No.: WO2008/082435
PCT Pub. Date: Jul. 10, 2008

(65) Prior Publication Data
US 2010/0013624 A1 Jan. 21, 2010

(51) Int. Cl.
*B60Q 1/40* (2006.01)
(52) U.S. Cl. .......... 340/477; 340/476; 340/475
(58) Field of Classification Search .......... 340/475, 340/476, 477; 362/465, 498; 307/10.8
See application file for complete search history.

(56) References Cited

U.S. PATENT DOCUMENTS

| | | | |
|---|---|---|---|
| 3,310,774 A | 3/1967 | Marian | |
| 3,732,539 A | 5/1973 | Easterly | |
| 4,030,066 A | 6/1977 | White | |
| 4,213,116 A | 7/1980 | Holtzman | |
| 4,358,751 A | 11/1982 | Roudebush, Jr. | |
| 4,907,844 A | 3/1990 | White | |
| 5,260,685 A * | 11/1993 | Parker | 340/477 |
| 5,438,314 A | 8/1995 | Evans | |
| 5,528,218 A | 6/1996 | Rigsby | |
| 5,581,235 A | 12/1996 | Hollstein | |
| 5,790,017 A | 8/1998 | Berryhill | |
| 6,020,813 A | 2/2000 | Harris | |
| 6,204,759 B1 | 3/2001 | Jahnke | |
| 6,876,300 B2 * | 4/2005 | Ponziani | 340/476 |
| 7,150,547 B2 * | 12/2006 | Okawa | 362/465 |
| 7,173,524 B2 * | 2/2007 | Ponziani | 340/476 |
| 7,408,455 B2 * | 8/2008 | Ponziani | 340/476 |
| 2004/0100373 A1 | 5/2004 | Ponziani | |
| 2005/0134447 A1 | 6/2005 | Su | |
| 2007/0282558 A1 * | 12/2007 | Sagisaka | 702/116 |

FOREIGN PATENT DOCUMENTS
JP 11301347 A 2/1999
JP 2003127763 A 8/2003
* cited by examiner

*Primary Examiner* — Van T. Trieu
(74) *Attorney, Agent, or Firm* — Martin Farrell; Michael Pruden

(57) ABSTRACT

A multi-function turn signal arrangement for an incorporating vehicle includes a user interface having a plurality of operator specifiable signaling modes including a right-direction-signal momentary blinking mode and a left-direction-signal momentary blinking mode. A controller is configured to receive input from the user interface indicative of an operator specified direction and mode and to initiate an automated signaling routine when one of the respective momentary blinking modes is specified and the controller determines that the incorporating vehicle is traveling at a speed within a predetermined speed range. The turn signal is maintained until a steering wheel of the incorporating vehicle is turned a predetermined amount in the signified direction and returned to the neutral, straight-ahead-driving position for a predetermined period of time and the vehicle remains in the predetermined speed range.

19 Claims, 1 Drawing Sheet

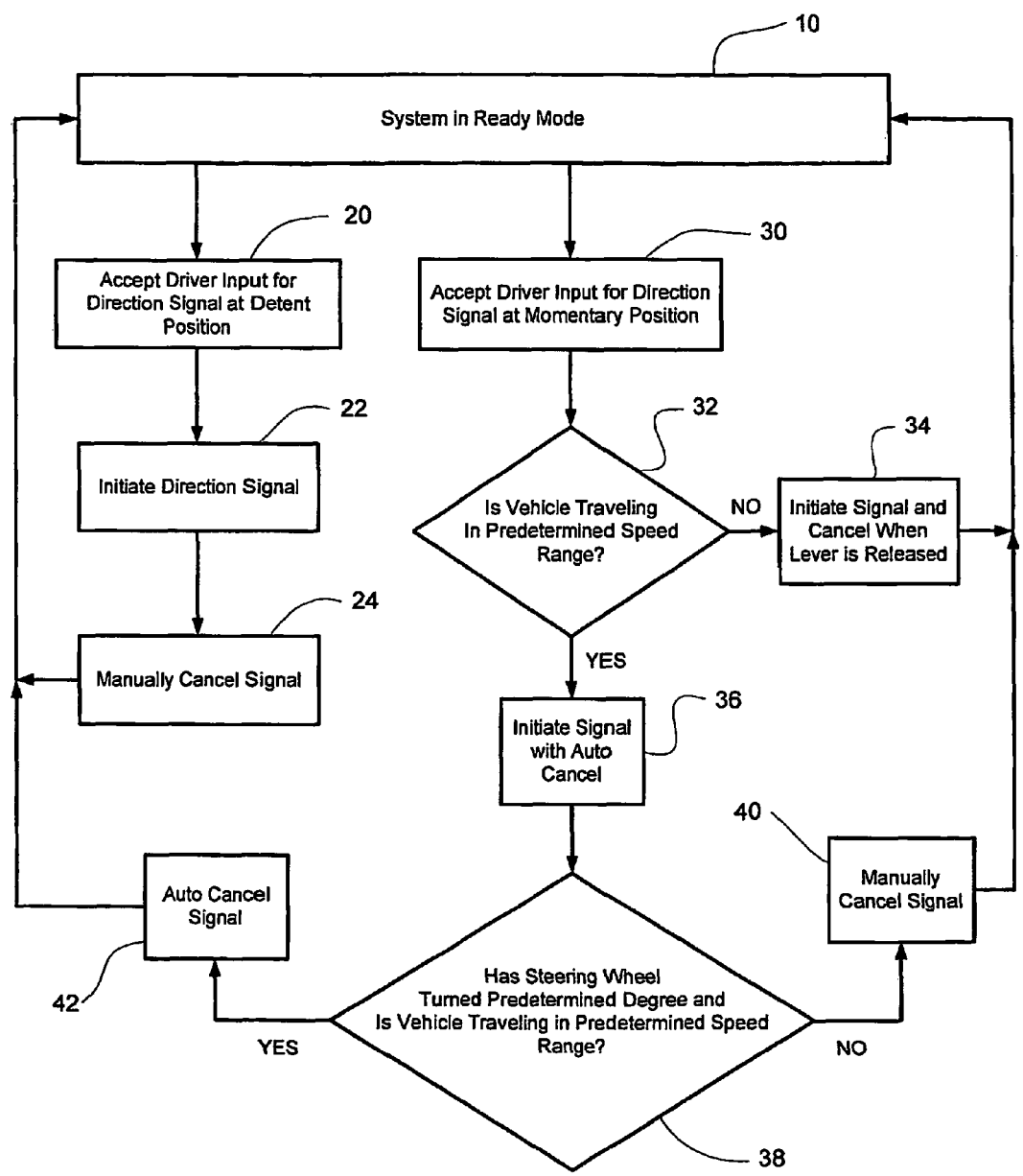

TURN SIGNAL DEVICE SELF CANCELLING FEATURE

FIELD

The present disclosure generally relates to the control of directional or turn signals in vehicles, and especially in commercial vehicles such as tractor trucks that may incorporate trailers or semi-trailers. A primary focus of the disclosure is on control aspects that integrate self/auto cancellation routines for turn signals with manually set signaling modes.

BACKGROUND and SUMMARY

While turn signal cancellation controls are well known, the present invention provides for improvements and enhancements over existing turn signal control strategies by providing for, among other things, controls that allow the driver to select between traditional and more advanced turn signal control feature. An example of such an advanced feature is the placement of a control lever in a position to effect signaling that will cancel when the steering wheel of the vehicle is detected to have returned to a neutral position from the direction for which the turn signal was activated. For example, a steering wheel execution of a right or left turn and subsequent return to a neutral or generally straight ahead alignment of the steering mechanism acts to cancel the turn signal. A further advanced turn signal mode is also provided that allows the driver to actuate a turn signal control that is sustained or locked as active until released by the driver.

When the driver selects the turn signal mode that provides for self/auto cancellation, further aspects of the present invention, including the specially tailored control strategies are implemented. The execution of turns and lane changes, especially by commercial vehicles of the nature of semi tractor trailer trucks, must be carefully made to appropriately accommodate the lengths of these vehicles. For safety, such turns must be signaled throughout the maneuver to assure awareness of other motorists. For driver convenience as well as safety, appropriate self/auto cancellation of the turn signal is a beneficial feature in that it relieves the driver of having to remember to disengage the executed signal and further prevents an unintended continuation of the signal for a prolonged period of time should the driver fail to disengage signal actuation.

The present invention meets these and other desired safety and convenience criteria by first providing means to effect activation of the self/auto cancellation mode of the turn signals by the driver. The self/auto cancellation is further implemented vis-à-vis computer-based control strategies that take into account vehicle speed and the degree by which the vehicle steering mechanism (steering wheel) is turned after a particular signaling mode is set. The time period that the steering wheel is allowed to return to the steering-neutral (straight ahead wheel alignment) position is also monitored as a threshold input for terminating the signaling sequence.

Importantly for both safety and driver convenience aspects, the selected turn signal mode of self/auto cancellation can as well be deactivated and the signaling routine cancelled manually by the driver by returning the selector control to the turn signal neutral position.

When the driver selects the maintained or locked turn signal position, the affected turn signal remains activated until manually deactivated by the driver by returning the turn signal selector to the neutral position. This mode can be contrasted with passenger vehicles which usually cancel signaling after the steering wheel has been turned a certain amount in the signaled direction and then allowed to resume the neutral position. This is not suitable in larger commercial vehicles, however, due to the wider range of steering wheel manipulation that is required, for instance, just to maintain course or when affecting a turn.

BRIEF DESCRIPTION OF THE DRAWINGS

The sole FIGURE is a diagrammatic representation, in the form of a flowchart, of the presently disclosed invention that automates directional signal control in a street vehicle under particular driving conditions.

DETAILED DESCRIPTION

As depicted in the FIGURE, the present disclosure describes a multi-function turn signal arrangement for an incorporating street vehicle. This may be any street vehicle such as passenger cars and the like, but particular utility is found in commercial vehicles such as tractor trucks that pull trailers or semi-trailers. The arrangement includes a user interface having a plurality of operator specifiable signaling modes including a momentary mode, a detent locked mode, and an automatic canceling mode. Those persons skilled in the relevant art will appreciate that an exemplary apparatus for a driver to indicate his or her desired mode is through a stalk-type turn signal indicator lever, which user interface for convenience will be referred to below as a lever. Alternatively, rocker switches, push buttons, or other interface devices could be used. It should also be appreciated that the described turn signal can exemplarily take the form of a traditional lighted design.

Due to the sophistication of the presently disclosed signaling control strategy, a controller is utilized that is configured to receive input from said user interface indicative of an operator specified signaling mode. In a particularly advantageous embodiment, the controller takes the form of a computer processor that may be stand-alone on the vehicle, or integrated as part of an otherwise existing processor in the including vehicle.

When the system is in a Ready Mode 10, that is, the vehicle engine is running and electrical systems are powered, the controller is configured to initiate a manual or automated signaling mode depending on indicated operator intent (as determined by manipulation of the lever) and sensed vehicle speed. The turn signal lever has five positions: a center, neutral position; a left momentary position; a right momentary position; a left detent position; and a right detent position.

According to a first aspect of the invention, a driver input placing the lever in either the left or right detent position 20 is received by the system and is used to generate a left or right turn signal. The detent positions are configured to hold the lever in place until manually released by the driver. The system initiates a turn signal 22 and the turn signal will remain active until the lever is manually returned to the neutral position, that is, manually canceled 24, by the operator. This function works at any vehicle speed. In addition, movement of the steering wheel does not release the lever from the detent position. Upon cancellation of the signal, the system then returns to Ready Mode.

According to a second aspect of the invention, a momentary mode is activated when the operator or driver moves the indicator stalk to one of the left or right momentary positions from the neutral position and the vehicle is traveling above a threshold speed. The threshold speed is set to be at the upper end of a speed range within which an automatic operation mode is active, which is explained below. The movement of the lever to one of the momentary positions signals a directional signal intent which is accepted by the system 30. The system monitors the vehicle speed 32 to determine whether the vehicle is in a predetermined speed range, which determines whether an automatic canceling routine or a momentary routine is initiated. If the vehicle is operating outside the predetermined speed range, the directional signal is generated only while the lever is manually held in the momentary position. The lever returns under bias to the neutral position when released, and the turn signal cancels 34.

A third aspect of the invention involves an automatic operation mode which includes an automatic signal canceling routine. The automatic operation mode is initiated when the lever is moved to one of the respective (left or right) momentary positions and the vehicle speed is within the predetermined speed range. When the driver moves the lever to one of the momentary positions, the driver input is accepted by the system 30. The system determines that the vehicle is traveling in the predetermined speed range 32. A turn signal is generated under the control of an automatic canceling routine 36. The presently disclosed strategy finds particular utility in a slower moving vehicle such as one involved in congested highway traffic. For example, the speed range may be above 5 miles/hour and not more than 25 miles/hour. Other speed ranges may be used as those of skill in the art may determine advantageous for the particular type of vehicle or duty cycle of the vehicle.

After it is confirmed that the incorporating vehicle is traveling within the predetermined speed range, the automated signaling routine continues the signal of the respectively indicated (left or right) directional signal until sensing conditions for canceling the signal. The conditions relate to the driver's operation of the steering wheel and the vehicle speed. The directional signal is maintained until a steering wheel of the vehicle is turned a predetermined amount in the signaled direction (for instance, rotated clockwise to affect a right direction turn after a right direction turn has been signaled) and then returned to the neutral, straight-ahead-driving position for a predetermined interval of time and-the vehicle remains in the predetermined speed range when the predetermined time period expires. The system monitors for these conditions 38 and, if met, the turn signal is canceled or terminated 42.

As an example, for a second aspect the predetermined speed range has an upper limit of approximately twenty-five miles per hour and a lower limit of five miles per hour. While not an absolute criteria, this speed range is indicative of a slower moving vehicle, not traveling at highway speeds. For vehicle speeds above the upper limit, which serves as the threshold, the second mode of the invention described above is activated, that is, a turn signal is activated for as long as the lever is held in the momentary position.

In a related aspect, the predetermined speed range has a lower limit, which in the described example is approximately five miles per hour. As intimated above, the presently disclosed control strategy is intended for implementation in slower moving vehicles that are not stopped, and which are not marshalling about in a loading facility or similar environment.

In an exemplary embodiment, the predetermined amount for turning the steering wheel in the signified direction is at least forty-five degrees. This effectively eliminates minor deviations of the steering wheel (for instance to maintain a lane tracking on a substantially straight section of roadway) from affecting implementation of the programmed turn signal control strategy.

The monitored predetermined period of time after the steering wheel has returned to the neutral, straight-ahead-driving position should be long enough to assure that the driver has, in fact, completed the turn and resumed straight forward driving. At the same time, the monitored time period must also minimize the period that a turn is being spuriously signaled, that is, that the driver has unintentionally initiated a turn but does not intend to maneuver the vehicle in the indicated direction. For example, a period of approximately five seconds is estimated to be sufficient In a further aspect, the automated signaling routine can also include manually canceling a signal by moving the lever to the opposite momentary position 40. Similarly, and optionally, the automated signaling routine can further comprise cancelling initiated blinking when the incorporating vehicle slows below approximately five miles per hour before expiration of the predetermined period of time.

The invention has been described in terms of exemplary steps and components, however, those skilled in the art will understand that substitutes and equivalents may be incorporated without departing from the scope of the invention as set forth in the appended claims.

What is claimed is:

1. A multi-function turn signal arrangement for an incorporating street vehicle, said arrangement comprising:
   a user interface having a plurality of operator specifiable signaling modes including a right-direction-signal momentary mode and a left-direction-signal momentary mode; and,
   a controller configured to receive input from said user interface indicative of an operator specified signaling mode and to initiate one of an automated signaling routine and a manual signaling routine, the controller configured to receive a signal indicative of a speed of an incorporating vehicle and to initiate the automated signaling routine if the vehicle is traveling at a speed within a predetermined speed range, and configured to monitor an angular position of a steering wheel of the incorporating vehicle, the automatic signaling routine comprising initiating blinking of a respectively indicated directional signal and canceling blinking of said directional signal upon receiving a signal indicating the steering wheel has turned a predetermined amount in the signified direction and returned to the neutral, straight-ahead-driving position and has remained in the neutral, straight-ahead position for a predetermined period of time.

2. The multi-function turn signal arrangement as recited in claim 1, wherein the controller is configured to cancel blinking of the directional signal upon further determining that the vehicle is in the predetermined speed range after the predetermined period of time expires.

3. The multi-function turn signal arrangement as recited in claim 1, wherein said controller is configured to initiate a manual signaling routine if the vehicle is traveling at a speed above the predetermined speed range, wherein blinking is maintained while the user interface is manually held in one of said right-direction-signal momentary mode and said left-direction-signal momentary mode.

4. The multi-function turn signal arrangement as recited in claim 1, wherein the predetermined speed range has an upper limit of approximately twenty-five miles per hour.

5. The multi-function turn signal arrangement as recited in claim 1, wherein the predetermined speed range has a lower limit of approximately five miles per hour.

6. The multi-function turn signal arrangement as recited in claim 1, wherein said predetermined steering wheel turned amount in the signified direction is at least forty-five degrees.

7. The multi-function turn signal arrangement as recited in claim 1, wherein said predetermined period of time for the steering wheel to be in the neutral, straight-ahead-driving position after being turned the predetermined amount is approximately five seconds.

8. The multi-function turn signal arrangement as recited in claim 1, wherein said automated signaling routine further comprises cancelling initiated blinking when an opposite direction signal momentary blinking mode is indicated before expiration of said predetermined period of time.

9. The multi-function turn signal arrangement as recited in claim 1, wherein said automated signaling routine further comprises cancelling initiated blinking when the incorporating vehicle slows below approximately five miles per hour before expiration of said predetermined period of time.

10. The multi-function turn signal arrangement as recited in claim 1, wherein said plurality of operator specifiable signaling modes further comprises a right manual only locked mode and a left manual only locked mode.

11. The multi-function turn signal arrangement as recited in claim 1, wherein said directional signal is at least one light.

12. A method for manually and automatically controlling a turn signal arrangement in an incorporating vehicle, the method comprising:
   accepting a user-generated indication from among a right-direction-signal momentary mode and a left-direction-signal momentary mode;
   monitoring a speed of an incorporating vehicle;
   initiating a directional signal in a manual, momentary signal mode if the speed of the incorporating vehicle is above a first threshold speed;
   initiating a directional signal in an automatically canceling signal mode if the incorporating vehicle is below the first threshold speed, wherein, the automatically canceling mode further comprises:
   monitoring an angular position of a steering wheel of the incorporating vehicle; and,
   canceling the directional signal upon the steering wheel being turned a predetermined amount in the signified direction and returned to a neutral, straight-ahead-driving position and remaining in the neutral, straight-ahead position for a predetermined period of time.

13. The method as recited in claim 12, wherein the automatically canceling signal mode further comprises canceling the directional signal upon further determining that the vehicle is in the predetermined speed range after the predetermined period of time expires.

14. The method as recited in claim 12, wherein said manual momentary signal mode comprises maintaining the directional signal while the user interface is manually held in one of the right-direction-signal momentary mode and the left-direction-signal momentary mode.

15. The method as recited in claim 12, wherein the first threshold speed is approximately twenty-five miles per hour.

16. The method as recited in claim 12, further comprising initiating the automatically canceling signal mode if the incorporating vehicle is below the first threshold speed and above a second threshold speed of approximately five miles per hour.

17. The method as recited in claim 12, wherein said predetermined steering wheel turned amount in the signified direction is at least forty-five degrees.

18. The method as recited in claim 12, wherein said predetermined period of time for the steering wheel to be in the neutral, straight-ahead-driving position after being turned the predetermined amount is approximately five seconds.

19. The method as recited in claim 12, wherein said automatically canceling signal mode further comprises accepting an opposite direction momentary mode before expiration of said predetermined period of time and canceling the directional signal.

\* \* \* \* \*